Figure 1:
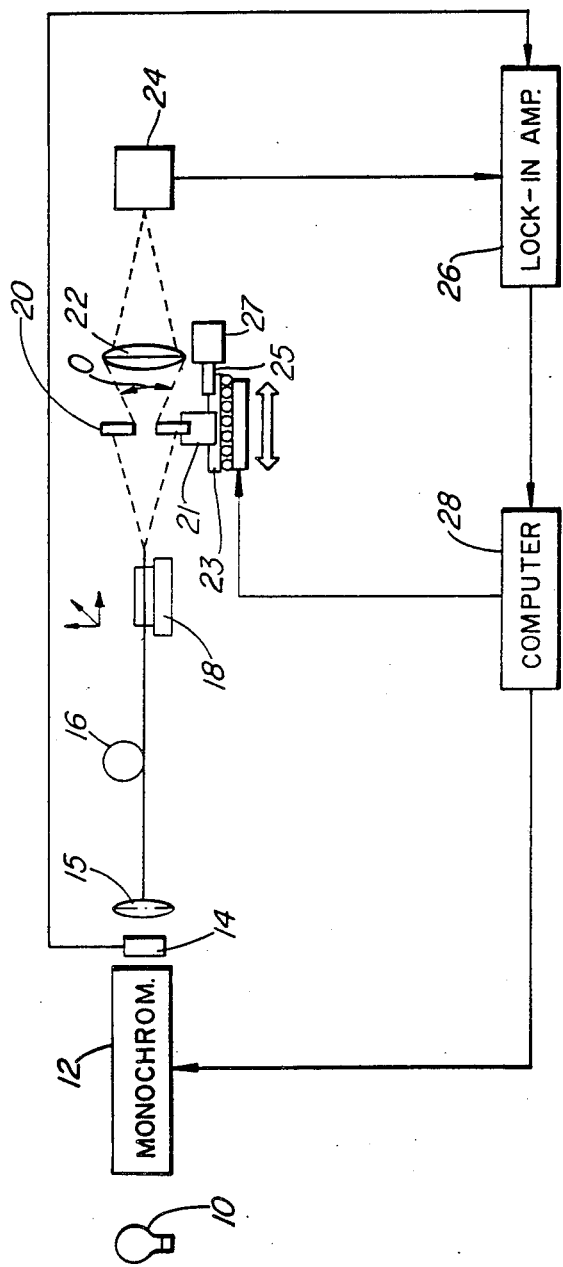

United States Patent [19]

Lowe et al.

[11] Patent Number: 4,636,071
[45] Date of Patent: Jan. 13, 1987

[54] METHOD AND APPARATUS FOR MEASURING SINGLE MODE FIBER MODE FIELD RADIUS

[75] Inventors: Richard S. Lowe, Kanata; Constantine Saravanos, Nepean, both of Canada

[73] Assignee: Northern Telecom Limited, Montreal, Canada

[21] Appl. No.: 797,064

[22] Filed: Nov. 6, 1985

[51] Int. Cl.$^4$ .............................................. G01N 21/84
[52] U.S. Cl. .................................. 356/73.1; 350/449; 356/225
[58] Field of Search ...................... 356/73.1, 225, 233, 356/234; 350/449, 266, 237 R

[56] References Cited

U.S. PATENT DOCUMENTS 4,565,445  1/1986  Alard et al. ......................... 356/73.1
4,586,816  5/1986  Stewart ............................... 356/73.1

*Primary Examiner*—Vincent P. McGraw
*Attorney, Agent, or Firm*—Stuart L. Wilkinson

[57] ABSTRACT

The fundamental-mode field radius 'w' is a key parameter in characterizing optical fibers. 'w' is a function of P, $\theta$ and $\lambda$ where P is the far-field power passing through a circular aperture subtending a solid angle of $2\theta$ at the fiber end face and $\lambda$ is the center wavelength of transmitted length. 'w' is derived by moving a fixed diameter aperture along an axis extending between the test fiber end surface and a photodetector so as effectively to vary $\theta$. At each location the power P incident on the photodetector and the corresponding acceptance angle $\theta$ are measured. A microprocesor is programmed to compute from the range of measured values of $\theta$ and P, the value of mode field radius for a particular transmission wavelength $\lambda$.

8 Claims, 2 Drawing Figures

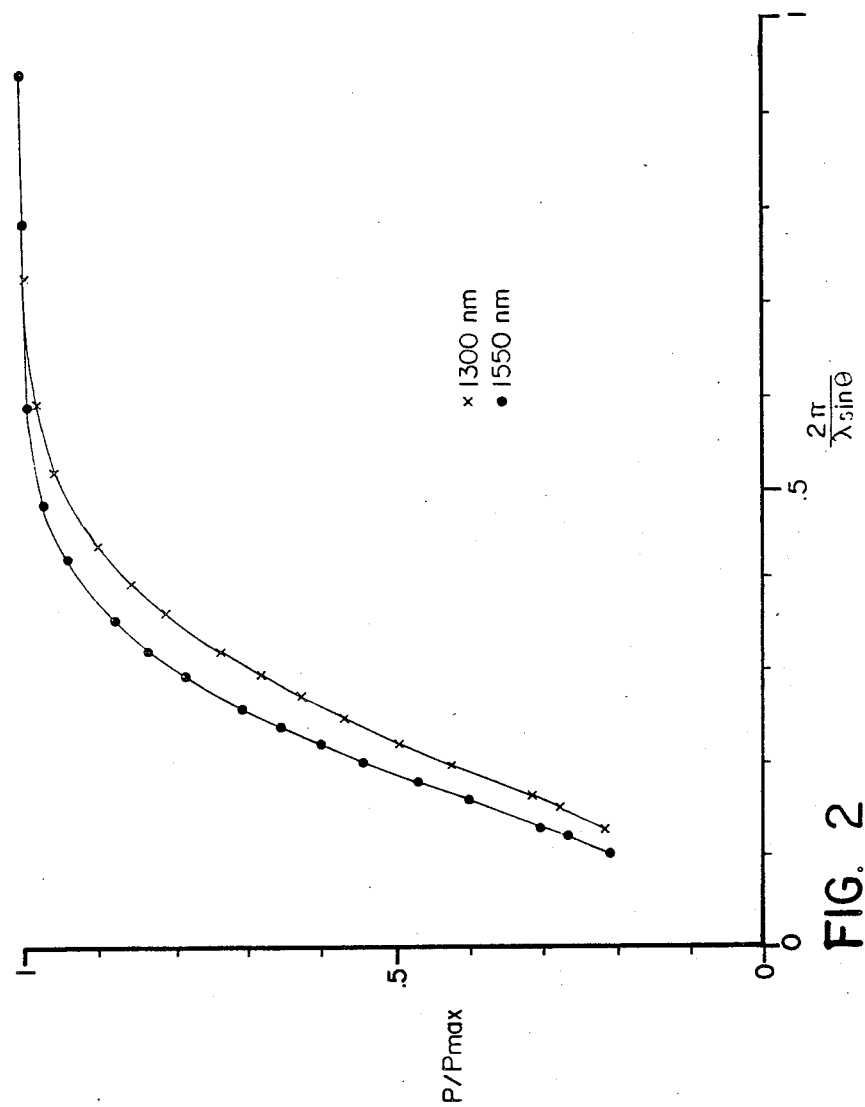

METHOD AND APPARATUS FOR MEASURING SINGLE MODE FIBER MODE FIELD RADIUS

This invention relates to a method and test set for measuring the fundamental mode field radius of a single-mode fiber.

The fundamental-mode field radius of a single-mode fiber is a key parameter in characterizing fibers. A knowledge of the spot size, which essentially is a measure of how centrally confined is the light intensity distribution within the fiber, can be used to predict certain fiber characteristics, such as splice loss and microbending loss.

The mode field radius 'w' has for some years been defined on the assumption that the near and far field distributions (i.e. the distributions respectively within a fiber and spaced from the fiber output face) are Gaussian in shape. On this assumption it can be shown that:

$$W_G = \left( \frac{\sqrt{2}\,\pi\tan\theta}{\lambda} \right)^{-1} \left[ -\log_e\left(1 - \frac{P(\theta)}{P_{max}}\right) \right]^{-2} \quad (1)$$

where
P is the power passing through an aperture which subtends an angle $2\theta$ at the fiber emitting face;
$P_{max}$ is the total emitted power; and
$\lambda$ is the center wavelength of the emitted light.

However the field only resembles a Gaussian distribution near the $LP_{11}$ cutoff i.e. the lower wavelength limit beyond which propagation within the fiber becomes multimode instead of single mode. Farther from cutoff the field is no longer Gaussian and in an expression for mode field radius proposed by Petermann (Electronics Letters, 19, No. 18, 1983):

$$W_p^2 = \frac{2P_{max}}{\left(\frac{2\pi}{\lambda}\right)^2 \int_o^\infty \frac{dP}{d\theta} \sin^2\theta\, d\theta} \quad (2)$$

In each of these cases the mode field radius 'w' is a function of P, $\theta$ and $\lambda$.

It is known to measure mode field radius with a variable aperture. However it is difficult to construct and operate a small aperture so that within a range of aperture sizes, the aperture retains its circularity.

According to one aspect of the present invention there is provided a method for determining the mode field radius 'w' of a single mode optical fiber comprising projecting light through the optical fiber, positioning a fixed diameter aperture in front of an exit face of the optical fiber in the far field pattern of light emitted therefrom, moving the aperture on the axis of emitted light through a series of acceptance angles $\theta$, measuring the power P passing through the aperture corresponding to said acceptance angles to obtain a relationship between P and $\theta$ and obtaining a value of mode field radius 'w' in terms of $\lambda$, P and $\theta$.

According to another aspect of the invention, there is provided a test set for determining the mode field radius 'w' of a single mode optical fiber comprising, projection means for projecting light of wavelength $\lambda$ through the fiber, a fixed diameter aperture located in front of an exit face of the optical fiber within a far field pattern of light emitted therefrom, carriage means for moving the aperture on the axis of light emitted from the fiber through a series of acceptance angles $\theta$, means for measuring the power P passing through the aperture corresponding to the acceptance angles, and signal processing means for deriving a value of w in terms of $\lambda$, $\theta$ and P.

Preferably the projection means comprises a light source and a monochromator for wavelength selection. The carriage means can comprise a mounting for a body defining said aperture, a linear track parallel to the axis of the fiber, a bearing between said mounting and the linear track, and a stepper motor for driving the mounting along the track. The measuring means can comprise a photodetector such as an InGaAs PIN photodiode, an amplifier for amplifying the photodiode output and a lens to focus light passed by said aperture onto the photodiode. To improve signal to noise ratio of the measuring means, the apparatus can further include a chopper for establishing an AC component on light projected into the fiber, the amplifier being a lock-in amplifier tuned to the frequency of said chopper. Said signal processor can have a first output to control the stepper motor, the processor being programmed to move said carriage through a predetermined sequence of steps. The processor can have a second output to the monochomator whereby to vary the output wavelength within a predetermined range.

An embodiment of the invention will now be described by way of example with reference to the accompanying drawings in which:

FIG. 1 shows a block schematic view of a test set according to the invention; and FIG. 2 is a graphical representation of far field output power from a fiber end face as a function of acceptance angle $\theta$ at spaced wavelengths 1300 and 1550 nanometers.

Referring in detail to FIG. 1, there is shown a quartz-halogen light source 10 emitting into a monochromator 12. The monochromator transmits only a narrow band of wavelengths, the monochromator output being modulated by a chopper 14 set to a frequency of 400 Hz. The monochromator output is directed through a focussing lens 15 to one end of a single mode fiber 16 under test. The remote end of the fiber is cleaved to produce a cleave angle less than 1° and is accurately fixed to a supporting pedestal 18 with an end portion of the fiber extending linearly along a predetermined axis. Spaced from the end of the fiber is a rigid metal disc 20 having a circular aperture of radius 1.5 millimeters. The lower edge of the disc 20 is mounted on a vertical post 21 which in turn is fixed to a slide 23 whose axis of motion is co-linear with the fiber-detector optical axis. A movable portion of the slide 23 is driven axially by a stepper motor driven micrometer 25. The stepper motor 27 is bolted to a separate bearing slide (not shown) to allow it to traverse axially as the micrometer drives the aperture.

The pedestal 18 and the disc supporting structure are both mounted on micromanipulators (not shown) to permit accurate axial alignment of the fiber end and the apertured disc.

For a single mode fiber having a core diameter of 9 microns and a cladding diameter of 125 microns, the apertured disc 20 is spaced from the fiber end by about 50 millimeters. Beyond the apertured disc 20 is a pair of lenses 22 which are coated to reduce reflection and are achromate to minimize chomatic aberration. The lenses focus far field light emitted by the fiber onto an InGaAs PIN photodiode 24. The output of the photodiode is taken to a lock-in amplifier 26 which is synchronized with the chopper frequency.

The amplifier output is taken to a microprocessor 28 which has outputs to both the monochromator 12 to vary the propagation wavelength and to the stepper motor 23 whereby the apertured disc 20 can be stepped axially through a predetermined sequence to change angle $\theta$.

In use, light of narrow spectral width is directed into the fiber 16 and is emitted from the fiber remote end where it diverges towards the aperture. Only a certain fraction P of the total output light $P_{max}$ incident on the apertured disc 20 is directed onto the photodetector 24 and this produces an electrical output which is amplified before being directed to the microprocessor 28. At the microprocessor a detected light P corresponding to the aperture position and thus to a predetermined acceptance angle $\theta$ is measured. Thus for a particular wavelength $\lambda$, a range of power values (P$\theta$) corresponding to a range of acceptance angles $\theta$ are derived.

As previously mentioned, the mode field radius 'w' can be derived using a number of expressions for the near- and far-field intensity.

The most commonly used assumes a Gaussian far-field distribution from which a mode field radius $w_g$ can be derived thus $$W_G^2 = 2\left(\frac{2\pi\tan\theta}{\lambda}\right)^2 \log\left(1 - \frac{P(\theta)}{P_{max}}\right) \quad (3)$$

A more accurate expression appears to be that proposed by Petermann, where the Petermann mode field radius:

$$W_p = \frac{2P_{max}}{\left(\frac{2\pi}{\lambda}\right)^2 \int_o^\infty \frac{dP}{d\theta} \sin^2\theta d\theta} \quad (4)$$

This expression is a function of dP/d$\theta$ and therefore the mode field radius cannot be derived (as for a Gaussian assumption) by a single measurement of P and $\theta$. For deriving the mode field radius where 'w' is a function of dP/d$\theta$ a number of measurements of P and $\theta$ are taken following successive repositioning of the apertured disc.

In practising the method, an accurate numerical calculation of 'w' requires at least 30 data points corresponding to 30 step positions of the apertured disc. This relatively large number of measurements is easily accomplished using microprocessor control to attain precise stepping of the motor 23 and processing of inputs from the photodiode 24.

Referring to FIG. 2 there is shown the normalized power $P/P_{max}$ as a function of $(2\pi/\lambda)\sin\theta$ at wavelengths of 1300 and 1550 nanometers for a particular test fiber. The Petermann mode field radius $w_p$ derived from the illustrated curves in respect of light at 1550 nanometers for example was 5.85 microns. This compares with a mode field radius $w_G$ of 6.18 microns obtained assuming a Gaussian distribution.

Although in the embodiment described, a quartz-halogen light source and a monochromator are used to generate light of narrow spectral width, the combination can be replaced by a series of switchable lasers at spaced wavelengths.

What is claimed is:

1. A method for determining the mode field radius 'w', of a single mode optical fiber comprising projecting light of wavelength $\lambda$ through the optical fiber, positioning a fixed diameter aperture in front of an exit face of the optical fiber in the far field pattern of light emitted therefrom, moving the aperture on the axis of emitted light through a series of acceptance angles $\theta$, measuring the power P passing through the aperture corresponding to said acceptance angles, and obtaining a value of mode field radius in terms of $\lambda$, P and $\theta$.

2. A test set for determining the mode field radius 'w', of a single mode optical fiber comprising projection means for projecting light through the fiber, a fixed diameter aperture located in front of an exit face of the optical fiber within a far-field pattern of light emitted therefrom, carriage means for moving the aperture on the axis of light emitted from the fiber through a series of acceptance angles $\theta$, means for measuring the power P passing through the aperture corresponding to the acceptance angles, and signal processing means for obtaining a value of mode field radius 'w' in terms of $\lambda$, P and $\theta$.

3. A test set as claimed in claim 2 in which the projection means comprises a light source and a monochromator for wavelength selection.

4. A test set as claimed in claim 2 in which the carriage means comprises a mounting for a body defining said aperture, a linear track parallel to the access of the fiber, a bearing between said mounting and the linear track, and a stepper motor for driving the mounting along the track.

5. A test set as claimed in claim 4 wherein the measuring means comprises a photodetector, an amplifier for amplifying the photodetector output, and a lens to focus light passed by said aperture onto the photodetector.

6. A test set as claimed in claim 2 further comprising a chopper for establishing an AC component on light projected into the fiber and a lock-in amplifier tuned to the frequency of said chopper, the chopper and the lock-in amplifier operable to improve signal-to-noise ratio of the measuring means.

7. A test set as claimed in claim 2, said signal processor having a first output to control the stepper motor, the signal processor being programmed to move said carriage through a predetermined sequence of steps.

8. A test set as claimed in claim 7, the signal processor having a second output to the monochromator whereby to vary the output wavelength within a predetermined range.

* * * * *